US008389936B2

(12) United States Patent
Freitag et al.

(10) Patent No.: US 8,389,936 B2
(45) Date of Patent: Mar. 5, 2013

(54) METHOD FOR INSPECTING A SAMPLE (75) Inventors: Bert Henning Freitag, Eindhoven (NL); Georg Alexander Rosenthal, Kempen (DE); Daniel Woodrow Phifer, Jr., Eindhoven (NL)

(73) Assignee: FEI Company, Hillsboro, OR (US)

( * ) Notice: Subject to any disclaimer, the term of this patent is extended or adjusted under 35 U.S.C. 154(b) by 202 days.

(21) Appl. No.: 12/833,750

(22) Filed: Jul. 9, 2010

(65) Prior Publication Data
US 2011/0006208 A1     Jan. 13, 2011

(30) Foreign Application Priority Data

Jul. 13, 2009   (EP) .................................... 09165269

(51) Int. Cl.
G21K 5/10      (2006.01)
G21K 5/00      (2006.01)
G21K 7/00      (2006.01)
(52) U.S. Cl. ............... 250/307; 250/440.11; 250/442.11
(58) Field of Classification Search .................. 250/306, 250/307, 310, 311, 440.11, 442.11
See application file for complete search history.

(56) References Cited

U.S. PATENT DOCUMENTS

| | | | |
|---|---|---|---|
| 3,903,324 A * | 9/1975 | Gukelberger et al. ........ 438/659 |
| 5,091,651 A | 2/1992 | Hokke | |
| 5,321,977 A * | 6/1994 | Clabes et al. ................... 73/105 |
| 5,986,270 A | 11/1999 | Bormans et al. | |
| 6,211,527 B1 | 4/2001 | Chandler | |
| 6,268,608 B1 | 7/2001 | Chandler | |
| 7,462,830 B2 * | 12/2008 | Terada et al. .................. 250/311 |
| 7,476,872 B2 * | 1/2009 | Terada et al. ............ 250/442.11 |
| 7,491,934 B2 * | 2/2009 | Jesse et al. ..................... 250/310 |
| 7,544,938 B1 | 6/2009 | Stewart et al. | |
| 2005/0173631 A1 * | 8/2005 | Ray et al. ....................... 250/307 |
| 2008/0067374 A1 * | 3/2008 | Ono et al. ...................... 250/310 |
| 2008/0102224 A1 | 5/2008 | Blackwood et al. | |
| 2008/0179518 A1 | 7/2008 | Creemer et al. | |
| 2008/0308731 A1 * | 12/2008 | Nishiyama et al. ........... 250/310 |
| 2009/0166536 A1 * | 7/2009 | Suga et al. ..................... 250/307 |
| 2009/0302224 A1 * | 12/2009 | Frank et al. .................... 250/362 |
| 2009/0302234 A1 * | 12/2009 | Terada et al. ............. 250/442.11 |
| 2009/0326866 A1 | 12/2009 | Stewart et al. | |

OTHER PUBLICATIONS

Kasama, Takeshi, et al., "A Versatile Three-Contact Electrical Biasing Transmission Electron Microscope Specimen Holder for Electron Holography and Electron Tomography of Working Devices," Mater. Res. Soc. Symp. Proc., 2006, 5 pgs, vol. 907E.

Sekitani, Tsuyoshi, et al., "Organic Transistors Manufactured Using Inkjet Technology with Subfemtoliter Accuracy," Proceedings of the National Academy of Sciences, Apr. 1, 2008, pp. 4976-4980, vol. 105, No. 13.

Creemer, J.F., et al., 'Atomic-Scale Electron Microscopy at Ambient Pressure,' Ultramicroscopy, 2008, pp. 993-998, vol. 108.

* cited by examiner

*Primary Examiner* — Bernard E Souw
(74) *Attorney, Agent, or Firm* — Scheinberg & Associates, P.C.; Michael O. Scheinberg (57) ABSTRACT

The invention describes a method for inspecting samples in an electron microscope. A sample carrier 500 shows electrodes 504, 507 connecting pads 505, 508 with areas A on which the sample is to be placed.

After placing the sample on the sample carrier, a conductive pattern is deposited on the sample, so that voltages and currents can be applied to localized parts of the sample.

Applying the pattern on the sample may be done with, for example, Beam Induced Deposition or ink-jet printing.

The invention also teaches building electronic components, such as resistors, capacitors, inductors and active elements such as FET's in the sample.

13 Claims, 9 Drawing Sheets

METHOD FOR INSPECTING A SAMPLE

The invention relates to a method for inspecting a sample with a particle-optical apparatus, the apparatus inspecting the sample with a beam of particles, the method comprising:
- providing a sample carrier equipped with electrodes,
- providing a sample,
- placing the sample on the sample carrier,
- introducing the sample in the particle-optical apparatus,
- inducing a voltage difference or a current in the sample,
- irradiating the sample with the beam of particles, and
- detecting particles transmitted through the sample, The invention also relates to a sample carrier equipped to perform the method according to the invention.

Such a method is known from U.S. Pat. No. 5,091,651

In a Transmission Electron Microscope (TEM) a thin sample is irradiated with a beam of electrons with an energy of, for example, between 80-300 keV. The sample is sufficiently thin to show transparency for these electrons. Some of the electrons are absorbed in the sample, some are elastically scattered (that is: their direction is changed while their energy is hardly changed) and some are inelastically scattered (that is: their direction and energy are changed). From the electrons transmitted through the sample information can be gathered from the sample. Such information can be spatially dependent transmittance of the sample, spatial dependent scattering and/or spatially dependent energy loss.

It is noted that also other information can be gathered, e.g. from electrons reflected from the sample, or by gathering secondary electrons emitted by the sample in response to the irradiation by the primary beam. Such secondary electrons typically have an energy between 0-50 eV. Also photons, such as X-rays, are generated by the bombardment of the sample with the primary beam, resulting in elemental information.

Typically the sample is placed on a sample carrier, also known as a grid, for support. The grid is typically a perforated foil of e.g. copper with a diameter of 3.05 mm and a thickness of between 20 and 50 µm. The sample is supported by the bars of the grid, while a part of the sample, overhanging the perforations, can be inspected by the electron beam. The sample carrier in turn is placed in a sample holder, which is used for positioning the sample with respect to the beam of electrons so that an area of interest of the sample can be centred round the beam for inspection.

It is mentioned that many TEM's can irradiate the sample with a non-focused beam or with a focused beam that is scanned over the sample. In the latter case the instrument is also referred to as a Scanning Transmission Electron Microscope (STEM). In the context of this application transmission electron microscopy includes scanning transmission electron microscopy.

U.S. Pat. No. 5,091,651 discloses a sample holder and sample carrier for use in a TEM. The sample holder and sample carrier can heat a sample while, for example, simultaneously running a current through the sample.

The sample holder comprises a cylindrical through-hole in which the sample carrier can be placed. The cylindrical hole shows a rim on which the sample carrier rests. The sample holder further comprises a heating wire for heating at least the part of the sample holder where the sample carrier resides.

The sample carrier shows a cylindrical outer diameter which fits into the cylindrical hole of the sample holder. It further shows a cylindrical bore for passing electrons unhindered. The sample can be placed on indents in the wall of the tube, perpendicular to the axis of the cylinder. The sample carrier further shows an insert with electrodes. The insert is open round the axis so as not to interfere with the transparency of the sample carrier round the axis. The electrodes contact parts of the sample, and in that way a voltage difference or a current can be induced between parts of the sample.

A problem with the known sample holder/sample carrier combination is that the points of connectivity to the sample are fixed in the construction. Thereby the position of the parts of the sample where a current or voltage may be induced are fixed by the design of the carrier/holder, and a change of these positions involves a change of carrier and/or holder. Also, the accuracy with which these areas can be determined is rather crude compared to the typical dimensions of the sample and/or features of the sample, the latter typically being less than several nanometers. It is noted that the optical resolution of a TEM is typically around one tenth of a nanometer (often referred to by an old standard of length, the Ångstrom).

It is mentioned that for certain applications it is known to induce a voltage difference between certain parts of a sample using manipulable probes that are brought into electrical contact with a part of the sample, see e.g. "A versatile three-contact electrical biasing transmission electron microscope specimen holder for electron holography and electron tomography and electron tomography of working devices", T. Kasama et al, Mater. Res. Soc. Symp. Proc. Vol. 907E, 2006 Materials Research Society. It describes a side entry specimen holder, where a sample is clamped between two electrodes. One of these electrodes may be an etched tungsten needle to form a movable contact.

A drawback of this design is that the positioning of the probes to microscopic accuracy is a time consuming process. Also the probes typically contact only a point on the sample, which may lead to e.g. unwanted high current density in the direct vicinity of the probe.

There is a need for an easy and flexible positioning of electrodes on the sample with microscopic accuracy.

To that end the method according to the invention is characterized in that, after placing the sample on the sample carrier and prior to the irradiation of the sample with the beam of particles, a conductive or semi-conductive pattern is applied to the sample, at least a part of said pattern in electric contact with the electrodes of the sample carrier.

The invention is based on the insight that, by forming a conductive or semi-conductive pattern on the sample itself and a part of the sample carrier, an electric connection can be made from the electrodes on the sample carrier to a region of interest on the sample.

In an embodiment of the method according to the invention applying the conductive or semi-conductive pattern and/or the electrodes comprises beam induced deposition or inkjet printing.

High resolution inkjet printing is known to deliver resolution of 5 µm or less, as described in e.g. "Organic transistors manufactured using inkjet technology with subfemtoliter accuracy" T. Sekitani et al., Proceedings of the National Academy of Sciences of the United States of America PNAS), Vol. 105, No 13, Apr. 1, 2008, pages 4976-4980. By applying a pattern using a conductive ink, a high resolution pattern with feature sizes of less than, for example, 5 µm, and even better positional accuracy can be deposited on the sample and sample carrier.

Even smaller feature size and higher positional accuracy can be obtained using beam induced deposition, in which a focused particle beam, such as an ion beam or an electron beam, is used to induce deposition from an adsorbed fluid. This fluid, the so-named precursor, is introduced in the evacuated specimen chamber of the particle beam apparatus by e.g. Gas Injection Systems and directed to the sample. This method is known per se to the person skilled in the art of ion microscopy, as are Gas Injection Systems. Suitable Gas Injection Systems are disclosed in, for example, FIGS. 3 and 4 of International Application WO00/22670 and the corresponding description.

Using these techniques structures with sub-micron features combined with sub-micron positional accuracy can be deposited on the sample.

In another embodiment of the method according to the invention the conductive or semi-conductive pattern is positioned with respect to the sample using registration with an optical microscope or a particle-optical microscope.

The positioning of the pattern with respect to (features of) the sample may be done using an optical microscope. As an alternative a particle-optical microscope, such as a Scanning Electron Microscope (SEM), a Scanning Transmission Electron Microscope (STEM), a Transmission Electron Microscope (TEM) or a Focused Ion Beam instruments (FIB) may be used. Such particle-optical microscopes are capable of imaging features of interest with resolutions of several nanometers to sub-nanometer resolution.

As Beam Induced Deposition (BID) can be performed with e.g. a SEM by Electron Induced Deposition (EBID) or a FIB by Ion Beam Induced Deposition (IBID), as described before, a pattern with sub-micron resolution can be applied with a positional accuracy of several nanometers in one instrument (e.g. the SEM or FIB).

In yet another embodiment of the method according to the invention the method further comprises milling at least one side of the sample.

Milling a sample enables modifying the shape of the sample, for example to reduce the thickness of a sample so that the sample becomes transparent to electrons by removing the surface until a suitable thickness is achieved, or for laying open sub-surface features of the sample. The milling may take the form of e.g. ion beam milling with a FIB. A suitable gas may be used to enhance the milling by enhanced etching. Such methods are known per se to the person skilled in the field of ion beam microscopy.

Preferably the conductive or semi-conductive pattern is applied after milling the at least on side of the sample.

In yet another embodiment of the method according to the invention a semiconductor element, a resistor or a capacitor or a piezo-electric part connects to the electrodes formed.

A semiconductor element, such as a diode or a varistor can be used, for example, to measure temperature or to heat a localized part of the sample to a predetermined temperature. A resistor can be used to define a potential or potential gradient on the sample, or to cause local heating of the sample, or (for a temperature dependent resistor) to measure the temperature or (for a PTC) to bring a local portion of the sample to a specific temperature. Likewise a capacitor can be used to study, for example, dielectrical properties, while piezoelectric elements can be used to induce mechanical stress to the sample during inspection (that is: while detecting the transmitted particles)

The semiconductor device, resistor, capacitor or piezoelectric part may be part of the sample as supplied, or may be formed on the sample, e.g. by inkjet printing using another material on the sample or by beam induced deposition using appropriate materials and/or appropriate thicknesses of the applied pattern.

In yet another embodiment of the method according to the invention the sample is a biological sample or a polymer.

Especially an electrically isolating or poorly conductive sample is well suited to make electrically conductive patterns thereon. Biological samples and polymers typically show a high resistivity.

In yet another embodiment of the method according to the invention the electrodes and/or the conductive or semi-conductive pattern are formed in a TEM.

As known to the person skilled in the art, a TEM (or a STEM) is best suited for forming an image of a sample using transmitted particles. Also other analysis techniques may be conducted on such instruments using the transmitted particles, such as Electron Energy Loss Spectroscopy.

By applying the pattern in the same instrument as in which the sample is observed, the pattern can be applied with the positional resolution with respect to features of the sample in the sub-nanometer range by first forming an image of the sample, finding features of interest and then applying the pattern with electron-beam induced deposition using the same electron beam, thereby eliminating positional uncertainties due to transferal of the frame of reference from one instrument to another.

Another benefit is that the sample need not be exposed to air, thereby avoiding, for example, oxidation of the sample after milling and/or, for example, oxidation of the applied pattern.

To enable, for example, beam induced deposition in the TEM or the STEM, the electrodes and/or the conductive pattern is preferably formed in an environmental cell within the electron microscope. In an environmental cell a very localized volume surround the sample, in which volume a gas can be admitted. This gas can be a precursor gas for EBID, thereby enabling deposition by a focused electron beam. Thereafter the gas can be exhausted and an image of the sample can be made without further deposition.

In yet another embodiment of the method according to the invention the electrodes and/or the conductive or semi-conductive pattern are applied prior to introducing the sample in the particle-optical apparatus.

Although in-situ application of the conductive pattern has advantages, ex-situ application may lead to increased through-put. Especially when positioning the pattern with a normal optical microscope and applying the pattern with, for example, inkjet printer techniques a pattern can be formed quickly. Automatic feature recognition for the positioning of the sample may further facilitate this.

In yet another embodiment of the method according to the invention the method further comprises forming an insulating pattern on the sample prior to forming the conductive or semi-conductive pattern on the sample, the insulating pattern forming an isolating layer between at least parts of the conductive pattern and the sample.

When the sample is not sufficiently isolating, but is either weakly conductive or that parts of the sample are conductive, it may be necessary to form an insulating layer on the sample prior to forming the conductive or semi-conductive pattern on the sample. In this way the pattern can be isolated from the sample or from parts of the sample, with the exception of the region of interest, where it may contact the sample.

In an aspect of the invention a sample carrier for carrying a sample, at least part of the sample carrier formed as a sheet with one or more edges for attaching or supporting a sample, is characterized in that the sample carrier shows electrodes extending to the one or more edges and extending to an area where the electrodes form contact pads for connecting with a sample holder.

A sample carrier typically shows a thin sheet of metal, such as copper, and shows one or more edges over which a sample is to be placed, the edges either part of a recess or part of a rim to which the sample is to be adhered. By now forming electrodes on such a sample carrier, one end of the electrode ending at the edge and the other at contact pads, a sample holder cooperating with said sample carriers can easily make contact with the electrodes, the electrodes in turn making contact with the conductive or semi-conductive pattern formed on a sample placed on the sample carrier.

The sample carrier may also be produced with Micro-Electro-Mechanical Systems (MEMS) technology, in which the sheet is formed of, for example, a semiconductor, and the recesses and electrodes are formed with, for example, lithographic processes.

It is noted that the recess or the place where the sample is attached on an outer edge of the sheet may extend in an electron transparent foil, such as a thin carbon foil or, for example, a thin silicon nitride foil. In this way a sample may be supported completely by an electron transparent foil. This transparent foil may cover the hole formed by a recess, but it may also extend from the outer edge to which the sample is to be placed.

In a further sample carrier according to the invention the sample carrier is formed as an environmental cell and the electrodes to which the electrodes extend and to which the sample is to be placed is in the environmental cell.

The use of environmental cell, also known as micro-reactors, for studying samples in an electron microscope at high pressure is known from "Atomic-scale electron microscopy at ambient pressure", J. F. Creemer et al., Ultramicroscopy 108 (2008), 993-998, more specifically FIG. 1 of said publication, hereby incorporated by reference. This publication discloses an embodiment of the environmental cell described in US patent application US2008/0179518.

By now adding electrodes to the environmental cell, one end of the electrodes ending at the position where the sample is to be placed, a sample carrier in the form of an environmental cell is formed where a sample may be studied at a pressure much higher than the pressure normally occurring in the electron microscope. Also, the use of an environmental cell enables the supply of precursor gasses to the sample, which enables the application of the conductive or semi-conductive pattern in situ.

Preferably the contact pads are place at the outside of the environmental cell so that they are accessible to a sample holder cooperating with the sample carrier.

BRIEF DESCRIPTION OF THE DRAWINGS

The invention is now described with reference to figures in which the identical reference numerals denote corresponding elements. Here:

FIGS. $1^a$ and $1^b$ schematically show prior art sample carrier,

FIGS. $2^a$ and $2^b$ schematically show prior art sample carriers with sample mounted thereon, FIG. 3 schematically shows a cut-through of a prior art sample carrier, FIG. $4^a$ schematically shows a first embodiment of a sample carrier according to the invention, FIG. $4^b$ schematically shows the sample carrier of FIG. $4^a$ with a sample placed thereon, on which a conductive pattern is applied, FIG. $5^a$ schematically shows a second embodiment of a sample carrier according to the invention, FIG. $5^b$ schematically shows a detail of the sample carrier shown in FIG. $5^a$ with a sample attached to it, FIG. $5^c$ schematically shows a detail of FIG. $5^b$, showing a detail of the conductive pattern applied to the sample, FIG. 6 schematically shows a prior art environmental cell for use in a TEM, FIG. $7^a$ shows an environmental cell for use with the method according to the invention, and FIG. $7^b$ schematically shows a part of the environmental cell of FIG. $7^a$, showing the electrodes to which the conductive pattern can be connected.

DETAILED DESCRIPTION OF PREFERRED EMBODIMENTS

Figure 1A:
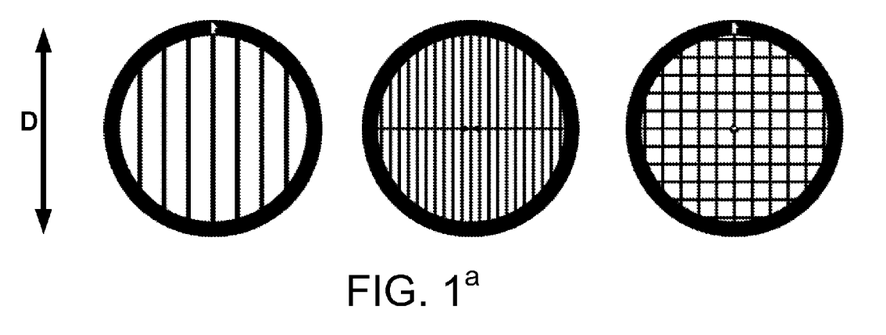

FIG. $1^a$ schematically shows prior art sample carriers as used in TEM microscopy.

Such sample carriers, commonly known as 'grids', are commercially available from, for example, SPI Supplies, West Chester, Pa., USA. A grid consists of a thin metal foil with a thickness of approximately 30 µm or less and an outer diameter D of approximately 3.05 mm. The metal may be, for example, copper, nickel, gold, gilded copper or gilded nickel. The outer part of a grid is an annulus of the metal. The hole of the annulus shows supporting structures in the form of, for example, bars or, for example, a mesh. Grids with different bar or mesh spacing are available. Such grids are often made with photo-lithographic techniques.

It is noted that also grids using a carbon coated plastic instead of metal are known. Samples placed on such grids are placed over the recesses between the grid and thereby supported.

Figure 1B:
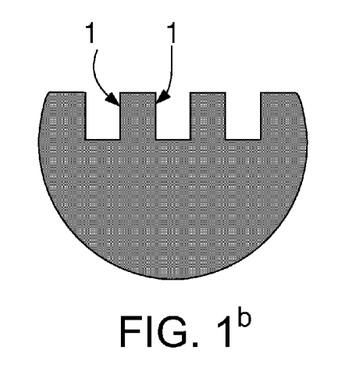

FIG. $1^b$ schematically shows another type of prior art sample carriers, in which the sample is to be attached to the outer edge of the sample carrier.

The sample carrier is a thin sheet of e.g. metal, such as copper, showing several outer edges 1 to which a sample may be adhered.

Figure 2A:
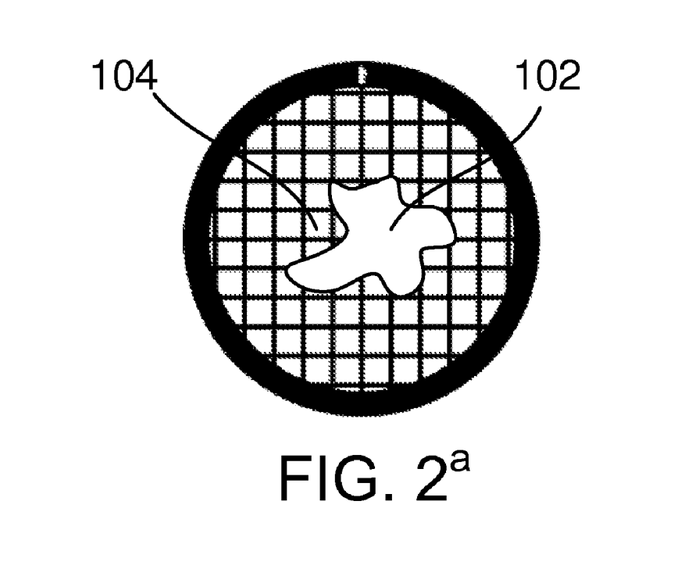

FIG. $2^a$ schematically shows a sample placed on the prior art sample carrier of FIG. 1a. The sample 102 is typically placed over one or more recesses 104 formed in the foil of the sample carrier.

Figure 2B:
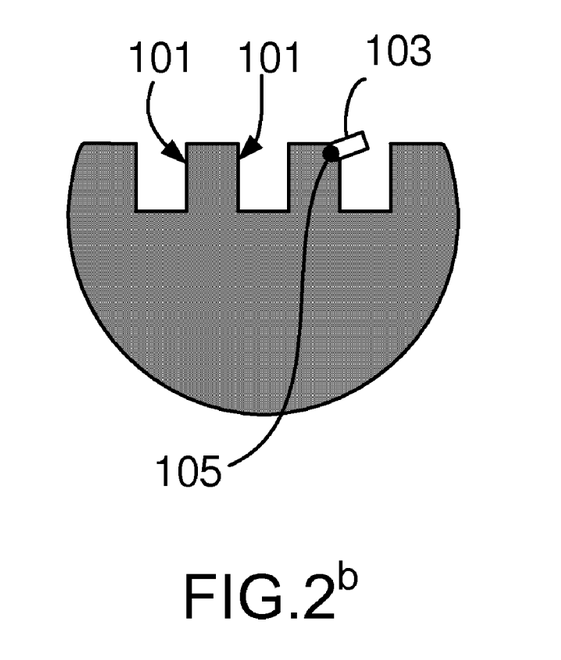

FIG. $2^b$ schematically shows a sample placed on the prior art sample carrier of FIG. 2a.

The sample 103, for example a sample taken form a semiconductor wafer, is typically a tile or wedge with largest diameters of, for example, tens of micrometers, and a thickness of, for example, 30 to 50 nm. A typically sample would thus be, for example 10*20 µm with a thickness of 30 nm. The sample is adhered to the outer edge of the sample carrier by depositing material 103 on a junction between the sample and the sample carrier. The adhesion may be done by e.g. depositing a drop of glue, but often material 103 is deposited by Beam Induced Deposition (BID). Both the preparation of such samples, the manipulation thereof and the adhering of such a sample to such a prior art sample carrier are known to the person skilled in the art.

In this way part of the sample is not supported by the sample carrier, and free for inspection. This type of sample carriers is used when inspecting thin samples 103 taken from a semiconductor wafer.

Figure 3:
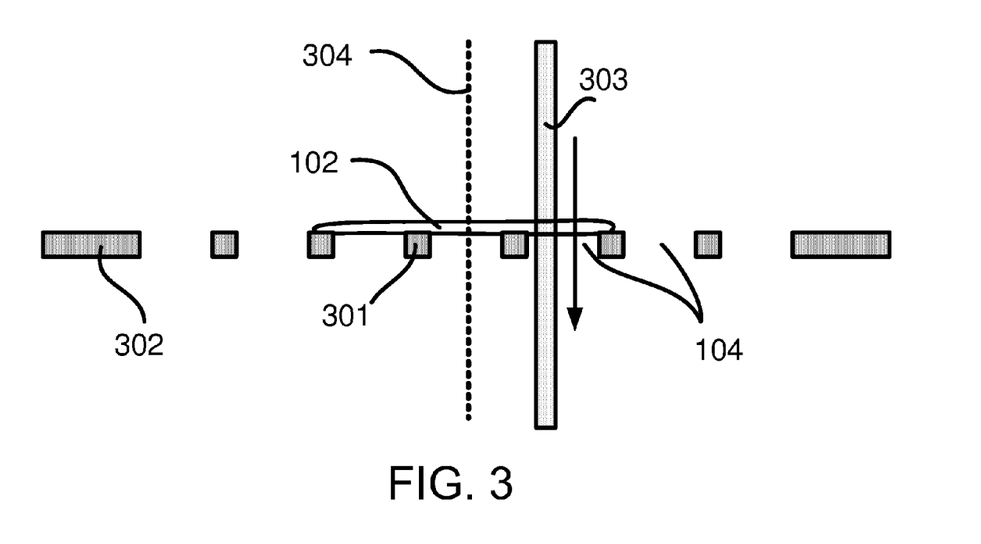

FIG. 3 schematically shows a cut-through of the prior art sample carrier of FIG. $1^a$, on which a sample is placed. A sample 102 is laid on the supporting structures 301, which may be for example be bars, hexagons or a rectangular or square mesh with recesses 104. The sample carrier shows symmetry around axis 304, The sample carrier shows an outer annulus 302, typically with an outer diameter of 3.05 mm, although other sizes are known to be used. The thickness of the sample carrier is typically 30 µm or less.

When inspecting the sample in a TEM, a beam of electrons 303 with an adjustable energy of, for example, between 60 to 300 keV, irradiates the sample. The beam irradiating the sample may be a parallel beam, or it may be a focused beam. A part of the electrons are absorbed in the sample, a part of the electrons are scattered away from the beam and a part of the electrons pass the sample unhindered. The electrons that pass through the sample (both the unscattered and the scattered electron) may be detected by a detector to form, for example, an image of the sample. The thickness of the sample may be as large as 1 μm, but often much thinner samples are used for the best image quality. When inspecting, for example, samples taken from a semiconductor wafer,—as is routinely done in the semiconductor industry—, the sample is often thinned to a thickness of less than 50 nm.

It is mentioned that to avoid charging of the sample and/or the sample carrier, the sample carrier is typically a metal foil, or a foil of a non conductive material such as a plastic, covered with a carbon coating for conductivity.

It is noted that inspection of the sample is preferably done at the areas 104 that are not supported by the sample carrier, as only there electrons can be transmitted. Therefore the transparency of the grid near the axis, where the sample typically resides, should be high, It is mentioned that also grids are used in which a thin film of carbon or a film of carbon coated plastic is used to span the recesses 104 between the bars or mesh so as to improve support for fragile samples without blocking the beam of electrons.

Figure 4A:
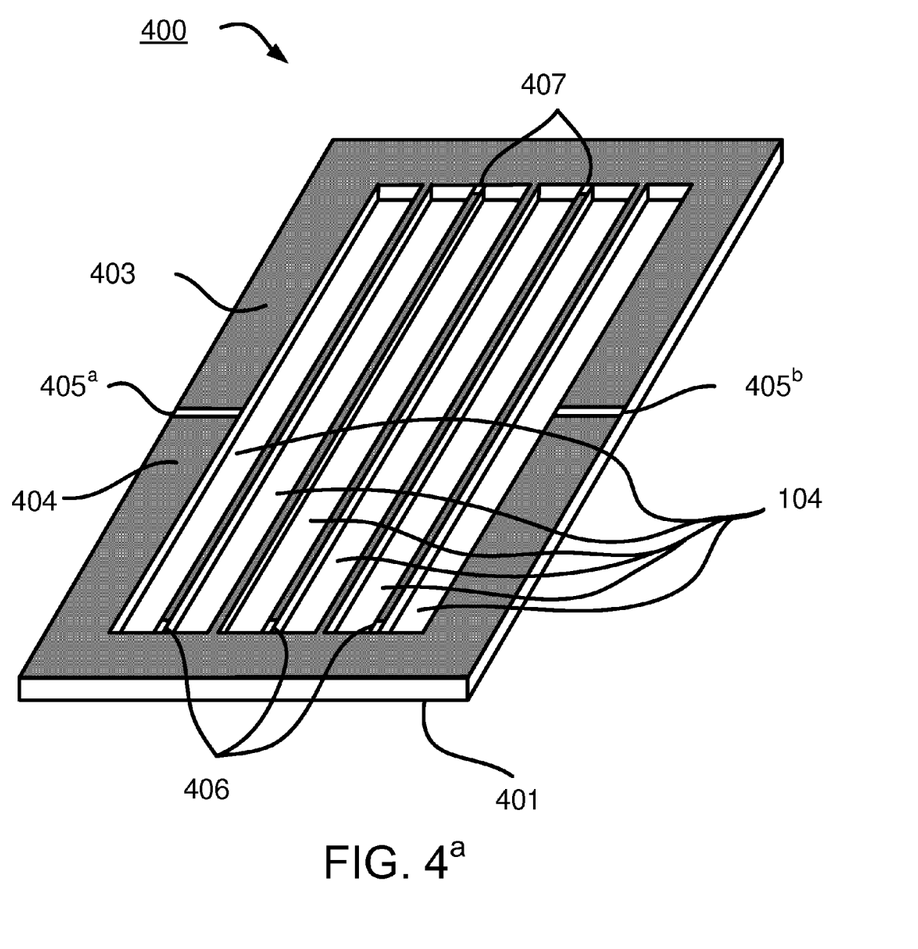

FIG. 4a schematically shows a sample carrier 400 according to the invention.

The sample carrier consists of a thin, rectangular piece 401 of insulating or poorly conductive material such as, for example, silicon. The rectangular piece shows a multitude of openings 104 for passing the particles unhindered and bars for supporting the sample when a sample is placed on the sample carrier. The surface of the piece is partly metallized, so that two electrodes 403 and 404 are formed, insulated from each other by gaps $405^a$, $405^b$, 406 and 407. As the gaps 406 and 407 are placed on different sides of the sample carrier, the metallization of some of the bars is part of electrode 404 and the metallization of other bars is part of electrode 403.

The sample carrier is preferably made with MEMS technology, in which the openings are etched in a chip of semiconductor material. However, other production methods may be used. This results in a structure that is capable of supporting a sample over, for example, a number of bars.

It is noted that, although the figure shows a rectangular sample carrier 401, this may have any shape, including round disks or parts thereof. Rectangles are more compatible with MEMS processes, while round disks are preferred when backward compatibility with prior art sample holders and sample carriers is demanded.

It is further noted that, although a sample carrier with only two electrodes 403 and 404 is shown, sample carriers with more than two electrodes can be made.

It is mentioned that the insulating parts between the electrodes may be covered with a weakly conductive coating to avoid charging, such as a carbon coating. The side walls 415 of the bars and/or the other side 414 of the sample carrier may likewise be covered with a slightly conductive coating to avoid charging.

Figure 4B:
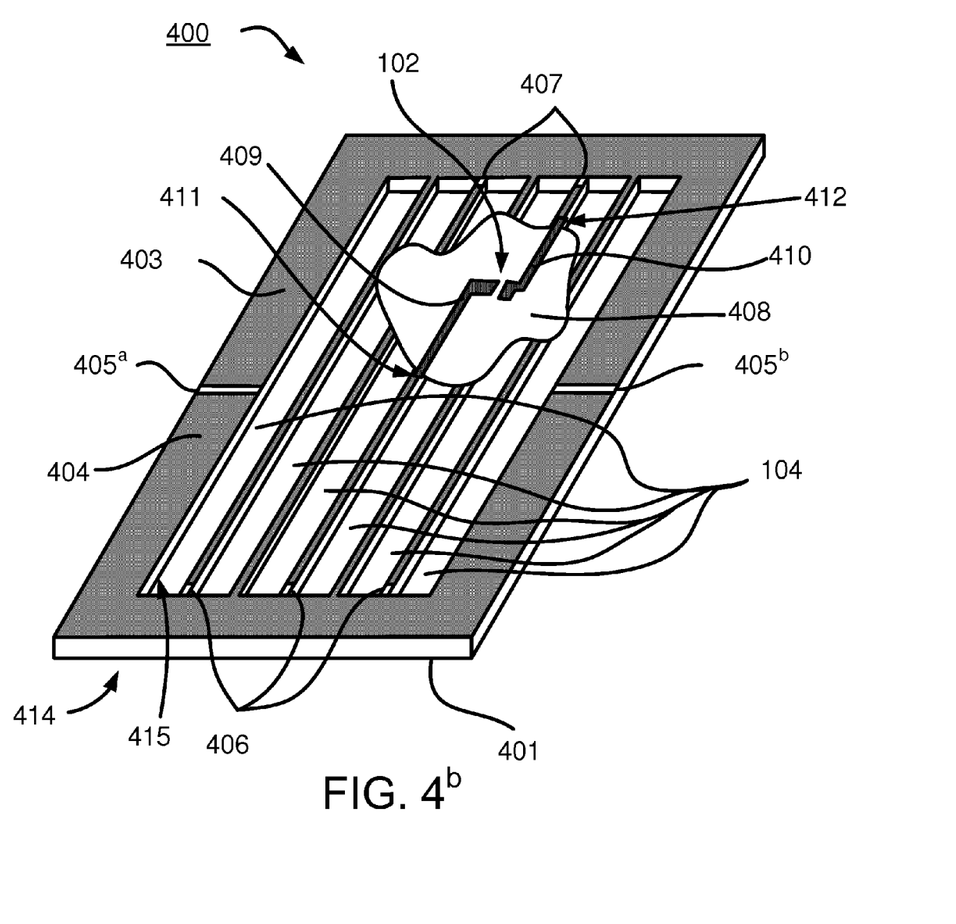

FIG. $4^b$ schematically shows the sample carrier of FIG. $4^a$, on which a sample is placed and on which a conductive pattern is applied.

A sample 408 is placed on the sample carrier 400. Conductive tracks 409 and 410 are formed by depositing a conductive material, such as gold, on the sample using, for example, inkjet printing or beam induced deposition. Both tracks have a distal end near an area of interest 413, while the other distal end of track 409 connects to electrode 404 at position 411 and the other distal end of track 410 connects to electrode 403 at position 412. In this way an electrical signal of the electrodes can be transported to the area of interest.

It is noted that, for example, a film of a resistive material may be applied between the tracks over or near the area of interest so as to cause highly localized heating and/or a device for measuring the temperature. Such a device can be a temperature dependent resistor, but may also be a diode or other semiconductor device.

It is further noted that the figure is not to scale. Typically the outer diameter of the sample carrier has a dimension of 1 or more millimeters, while the tracks may have smallest dimensions as small as 5 μm or less.

It is mentioned that the sample may be, for example, a biological sample or a polymer, which is in itself insulating, or it may be a semiconductor sample taken from a wafer, which in itself shows conductive parts, or another such sample showing local or general conductivity. In that case it may be attractive to place a pattern of insulating material on the sample prior to forming the conductive pattern on the sample, so that the conductive pattern is isolated from (parts of) the sample.

Forming the conductive pattern (for transporting electric signals from the sample carrier to a region of interest) and/or the insulating pattern (for isolating the conductive pattern from the sample) and/or resistive pattern (for e.g. local heating) can be done with e.g. inkjet printing techniques, with beam induced deposition (using e.g. a beam of photons, electron or ions).

Beam induced deposition is a technique well known to the person skilled in the art. Instruments for performing beam induced deposition are commercially available from, e.g. FEI Co., the assignee of the present application. Instruments for Electron Beam Induced Deposition (EBID)—equipped with a Scanning Electron Microscope (SEM) column—, or instruments for Ion Beam Induced Deposition (IBID)—equipped with an Focussed Ion Beam (FIB) column—are available, as well as instruments combining a FIB and a SEM column.

To that end a Gas Injection Systems as shown in FIGS. 3 and 4 of International Application WO00/22670 introduces a jet of precursor gas to the sample and sample carrier. Precursor gas molecules adsorb to the surface of the sample and sample carrier. By then locally irradiating the sample carrier and sample, the adsorbed precursor molecules dissociate and a conductive residue is left on the sample and sample carrier.

In this deposition methods a wide range of materials can be deposited on a substrate or work piece for many purposes. Such materials include Al, Au, amorphous carbon, diamond-like carbon, Co, Cr, Cu, Fe, GaAs, GaN, Ge, Mo, Nb, Ni, Os, Pd, Pt, Rh, Ru, Re, Si, $Si_3N_4$, $SiO_x$, $TiO_x$, and W. The material selected to be deposited depends on the application, including the composition of the underlying target surface, and the intended purpose of the deposition.

Commonly used deposition gasses include precursor compounds that decompose to, for example, deposit W, Pt, and Au. For example, W-hexacarbonyl [CAS number 14040-11-0] can be used to deposit tungsten (W), methylcyclopentadienyl Pt trimethyl [CAS number 1271-07-4] can be used to deposit platinum (Pt), and dimethyl Au acetylacetonate [CAS number 14951-50-9] can be used to deposit gold (Au). Many more precursor gasses for deposition, both organic and inorganic in nature, are known.

It is mentioned that a FIB may also use the focused ion beam to mill the sample. Precursor gases are known resulting in enhanced etching, such as $XeF_2$ and $H_2O$. GIS'ses can be used to introduce such gases as well, resulting in enhanced milling capabilities of such instruments. In this way the patterns can be applied with sub-micron precision as well as that the sample is, at least locally, trimmed to the required thickness and/or size for inspection in a TEM.

Figure 5A:
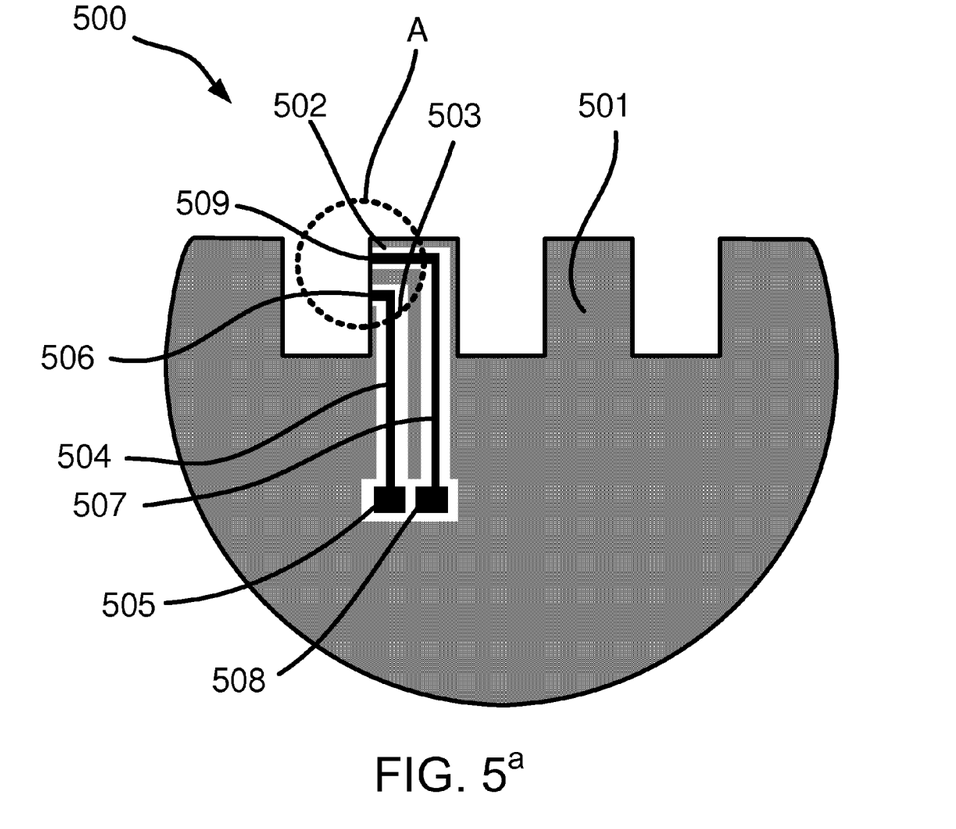

FIG. $5^a$ schematically shows a sample carrier 500 according to the invention.

FIG. $5^a$ can be thought to be derived from FIG. $1^b$. The semi-annular disk 501, with a thickness of for example between 30 and 100 μm, is made of, for example, a metal such as copper. On this thin copper sheet isolating layers 502 and 503 are formed. On these insulating layers two conductive tracks 504 and 507 are formed. Track 504 shows an end 506 ending at the position where a sample should be mounted, while the other end of the track ends in a pad 505 where a sample holder can contact the track. Likewise track 507 shows an end 509 where the sample should be mounted, and a pad 508 to be contacted by the holder.

Figure 5B:
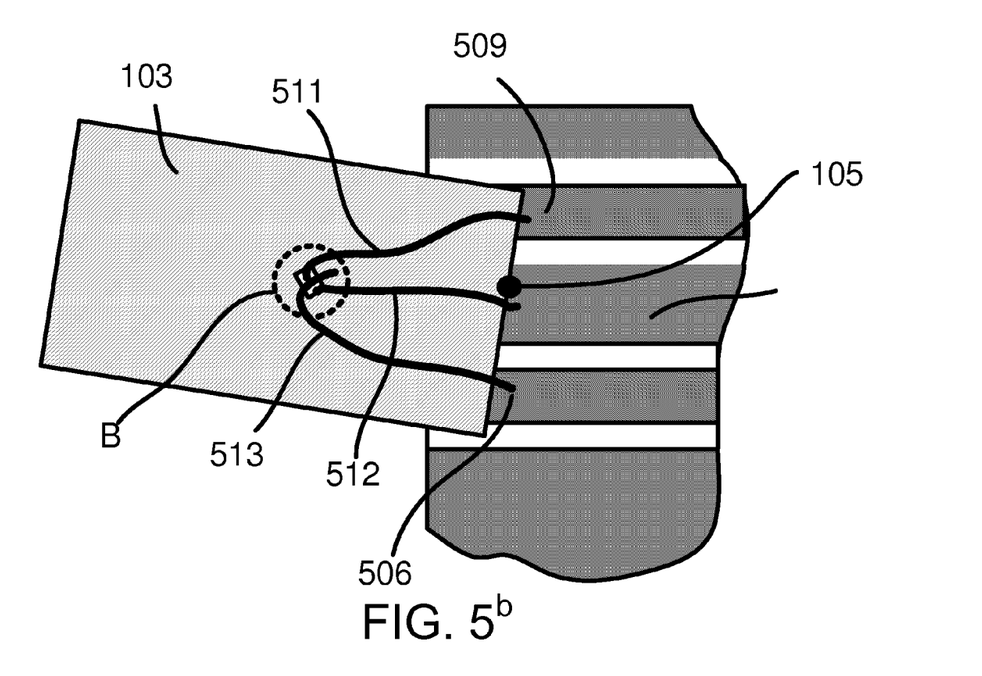

FIG. 5b schematically shows the area A of FIG. $5^a$.

The material of the sample carrier 501, and the conductive tracks 509 and 506 of the sample carrier are shown. The sample 103 is adhered to the sample carrier by depositing material 105 on a junction between the sample and the sample carrier. This may be done by depositing, for example, a drop of glue, or by Beam Induced Deposition (BID). After mounting the sample, conductive tracks 511, 512 and 513 are deposited on the sample, track 511 making contact with track 509 on the sample carrier, track 512 contacting the foil of the sample carrier, and track 513 contacting track 506 on the sample carrier.

In this way voltages and/or currents can be brought to an area of interest B.

Figure 5C:
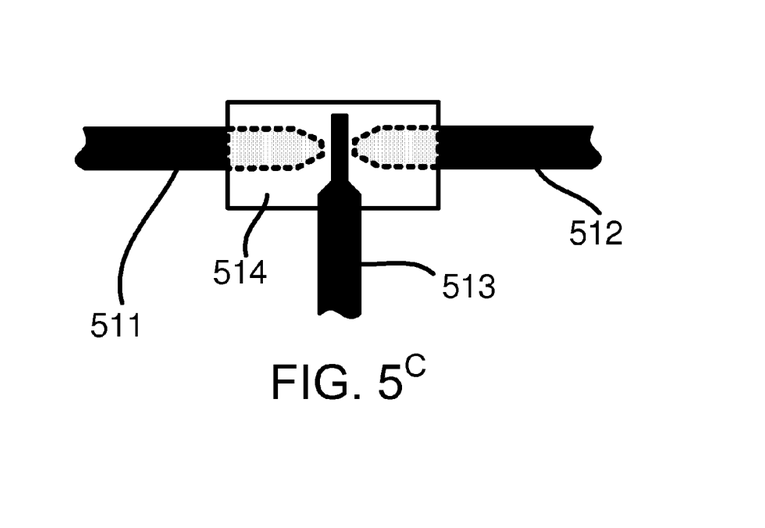

FIG. 5c schematically shows the area of interest B shown in FIG. 5b.

FIG. 5c shows that conductive tracks 511 and 512 end close together, and that an insulating layer 514 is placed over this area. On top of this conductive track 513 is placed. In this way an active element such as a field effect transistor (FET) may be formed on the sample locally.

Likewise the layer 514 can be, for example, a resistive layer, acting as a local heater.

Many other application are foreseen, including the local application of passive elements (resistors, capacitors, inductors), active elements (FET's, transistors, and photonic elements such as LED's) and others, such as piezoelectric elements Besides these elements, that may be in direct contact with the electrodes, the study of local effects may be improved by, for example, locally forming magnetic material guiding the magnetic flux formed by an inductor (pole pieces), or by forming materials with high dielectric constants.

When the process of deposition is performed in a TEM, then it is possible to mill the sample, deposit the conductive pattern and inspect the sample all in one instrument, without exposing the sample to air between any process steps. This eliminates, for example, oxidation or other chemical changes due to the exposure.

To deposit the conductive pattern the pressure near the sample should be larger than what is normally allowable in a TEM.

There are TEM's in which the volume around the sample may have a higher pressure, sufficiently high for performing BID and the like. Such a TEM's, also known as 'Environmental TEM' or ETEM, is commercially available from FEI Company, assignee of the present application. Differential pumping apertures limit leakage of the gas near the sample to other areas of the TEM where such high pressures are not allowable. The pressure around the sample may be sufficiently high to permit moist samples to be studied at a temperature of, for example, 4 degrees centigrade, at a (partial) water vapour pressure of approximately 8 mbar.

Another solution is to study the sample in a so-named environmental cell, that is: a small gas tight reactor in which the sample can be placed. The inner volume of such a reactor can be at a pressure of, for example, 1 bar, while the exterior is, for example, at a pressure of $10^{-3}$ mbar or less, being the typical pressure of the TEM vacuum chamber where the sample resides. The environmental cell further shows electron transparent windows through which the electron beam may pass.

Figure 6:
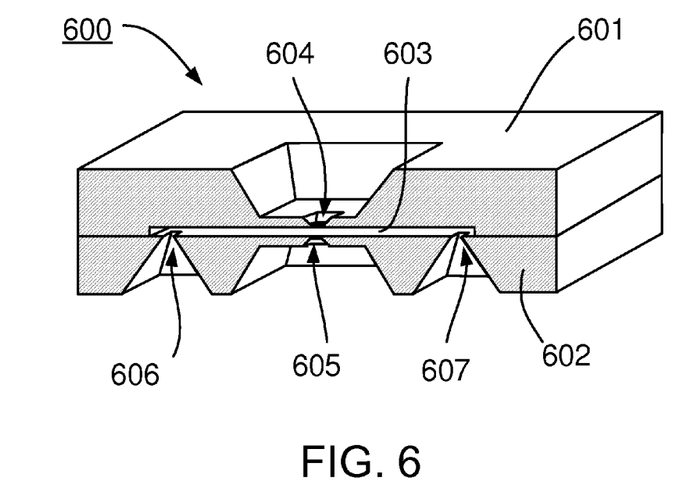

FIG. 6 schematically shows a prior art environmental cell, disclosed in shown in "Atomic-scale electron microscopy at ambient pressure", J. F. Creemer et al., Ultramicroscopy 108 (2008), 993-998, more specifically FIG. 1 of said publication, hereby incorporated by reference. This publication discloses an embodiment of the environmental cell described in US patent application US2008/0179518.

The environmental cell 600 disclosed comprises two silicon structures 601 and 602, also named dies, which are fused to each other. A thin gap defines a chamber 604 between the two dies in which a sample can be placed. The chamber shows two thin windows 604 and 605 that are transparent to electrons. A gas inlet 606 and a gas outlet 607 enable the admission of gas into the chamber when the environmental cell is placed in a vacuum, preferably the sample chamber of a TEM.

The sample is placed on the electron transparent window of one of the dies, and then the other die is placed over the sample. By then bonding, fusing or just pressing the dies together, an airtight seal of the chamber 603 to the outside is realized. The gas inlet and the gas outlet are likewise coupled to ports of a dedicated sample holder, as shown in FIG. $1^b$ of the mentioned publication.

In working the beam of electrons which is used in the TEM to inspect the sample passes through the electron transparent windows and the sample therein between.

Such an environmental cell is used, for example, to observe samples at high pressure, such as atmospheric pressure or at least a pressure in which dehydration of the sample is avoided.

Figure 7A:
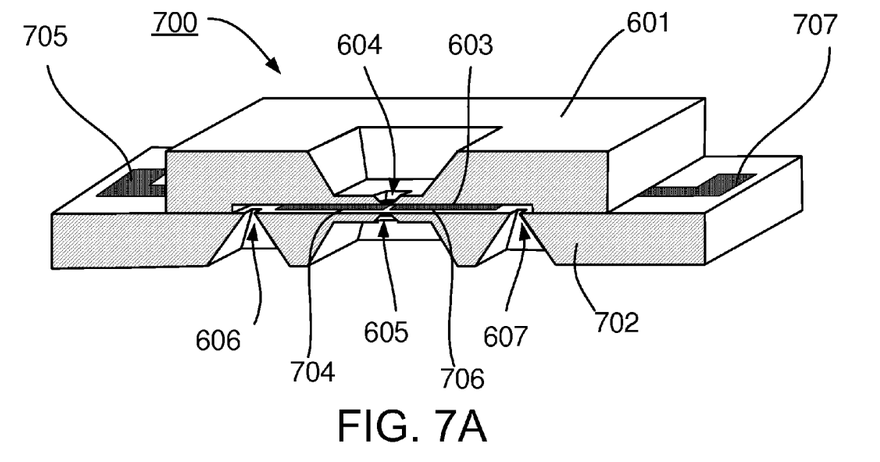

FIG. $7^a$ schematically shows an environmental cell for use with the method according to the invention.

The environmental cell can be thought to be derived from FIG. 6. The die that in working is positioned in the downstream direction of the electron beam, die 702, shows a metallization pattern with ends 704, 706 near the position where the sample should be placed. This metallization pattern forms two electrodes that end in to pads 705, 707 to be contacted by a sample holder outside the environmental cell.

Figure 7B:
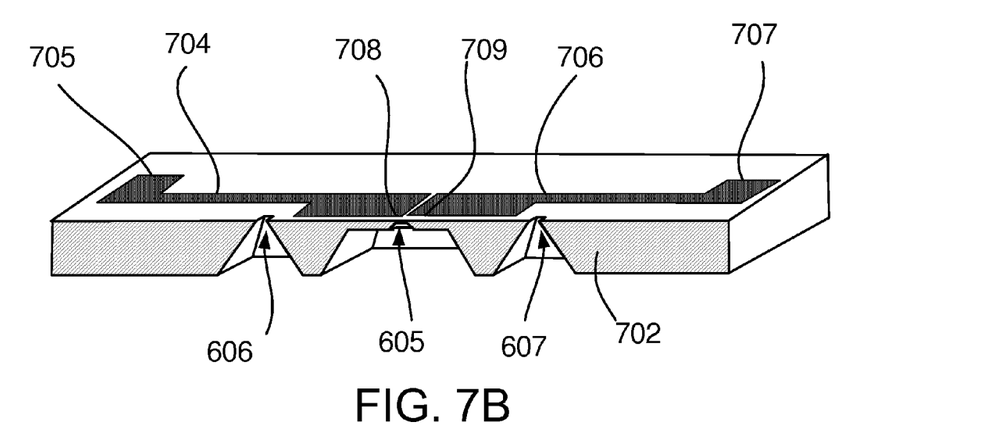

FIG. $7^b$ schematically shows a part of the environmental cell of FIG. $7^a$, showing the electrodes 704, 706 to which the conductive pattern can be connected.

FIG. $7^b$ shows die 702 as shown in FIG. $6^a$. The electrodes 704 and 706 end in to structures 708 and 709 that are separated by a small gap so that they are electrically insulated from each other.

By placing the sample over the electrodes (or close to the electrodes) and then placing and bonding the second die over the first die, the sample is placed in the environmental cell. The cell is then placed on a sample holder which connects the environmental cell to a gas inlet and -outlet (just as in the prior art environmental cell) and additionally also connects to the electrodes 704 and 706. The sample holder, holding the environmental cell, can then be introduced in the TEM. Using the TEM for imaging, features of interest can be found. An EBID precursor is then introduced in the environmental cell via the gas inlet, as a result of which a focused electron beam scanned over the sample causes deposition. In this way the TEM can form the conductive pattern in situ. By removing the precursor gas (by stopping the flow of precursor gas while pumping the exhaust of the environmental cell) the TEM can image the sample without causing further deposition. A current or a voltage can be applied to places of interest on the sample while imaging.

It is noted that the environmental cell of the prior art environmental cell also comprises electric contacts. These, however, are used for making contact with an electric heater and a temperature sensor formed on one of the dies and are not formed close to the position where the sample is to be mounted. The sample holder used for holding this prior art environmental cell is an example of a holder for cooperating with the sample carriers according to the invention.

We claim as follows:

1. Method for inspecting a sample with a particle-optical apparatus, the apparatus inspecting the sample with a beam of particles, the method comprising:
   providing a sample carrier equipped with electrodes,
   providing a sample;
   placing the sample on the sample carrier,
   introducing the sample in the particle-optical apparatus,
   inducing a voltage difference or a current in the sample,
   irradiating the sample with the beam of particles, and
   detecting particles transmitted through the sample,
   wherein, after placing the sample on the sample carrier and prior to the irradiation of the sample with the beam of particles, a conductive or semi-conductive pattern is deposited onto the sample, at least a part of said pattern in electric contact with the electrodes of the sample carrier.

2. The method of claim 1 in which applying the conductive or semi-conductive pattern and/or the electrodes comprises beam induced deposition or inkjet printing.

3. The method of claim 1 in which the conductive or semi-conductive pattern is positioned with respect to the sample using registration with an optical microscope or a particle-optical microscope.

4. The method of claim 1 the method further comprising milling at least one side of the sample.

5. The method of claim 4 in which the conductive or semi-conductive pattern and/or the electrodes are formed after milling at least one side of the sample.

6. The method of claim 1 in which a semiconductor device, a resistor or a capacitor or a piezo-electric part connects to the electrodes formed.

7. The method of claim 6 in which the semiconductor device, the resistor or the capacitor or the piezoelectric part is part of the sample.

8. The method of claim 6 in which the semiconductor device, the resistor or the capacitor or the piezoelectric part is formed on the sample.

9. The method of claim 1 in which the sample is a biological sample or a polymer.

10. The method of claim 1 in which the application of the electrodes and/or the conductive or semi-conductive pattern are formed in a transmission electron microscope.

11. The method of claim 1 in which the application of the electrodes and/or conductive or semi-conductive pattern are formed in an environmental cell.

12. The method of claim 1 in which the electrodes and/or the conductive or semi-conductive pattern are applied prior to introducing the sample in the particle-optical apparatus.

13. The method according claim 1 in which the method further comprises forming an insulating pattern on the sample prior to forming the conductive or semi-conductive pattern on the sample, the insulating pattern forming an isolating layer between at least parts of the conductive or semi-conductive pattern and the sample.

* * * * *